(12) United States Patent
Takagi et al.

(10) Patent No.: US 11,286,459 B2
(45) Date of Patent: Mar. 29, 2022

(54) CELL CULTURING METHOD USING NUCLEIC ACID-CONTAINING MEDIUM

(71) Applicant: Astellas Pharma Inc., Tokyo (JP)

(72) Inventors: Yasuhiro Takagi, Tokyo (JP); Takuya Kikuchi, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 581 days.

(21) Appl. No.: 15/576,441

(22) PCT Filed: May 26, 2016

(86) PCT No.: PCT/JP2016/065625
§ 371 (c)(1),
(2) Date: Nov. 22, 2017

(87) PCT Pub. No.: WO2016/190394
PCT Pub. Date: Dec. 1, 2016

(65) Prior Publication Data
US 2018/0155676 A1    Jun. 7, 2018

(30) Foreign Application Priority Data

May 27, 2015 (JP) .............................. JP2015-107147

(51) Int. Cl.
| | |
|---|---|
| C12N 5/00 | (2006.01) |
| C07K 16/00 | (2006.01) |
| C12P 21/00 | (2006.01) |
| C12N 5/10 | (2006.01) |
| C12N 1/00 | (2006.01) |
| C12P 21/02 | (2006.01) |

(52) U.S. Cl.
CPC ............ *C12N 5/0018* (2013.01); *C07K 16/00* (2013.01); *C12N 1/00* (2013.01); *C12N 5/10* (2013.01); *C12P 21/00* (2013.01); *C12P 21/02* (2013.01); *C12N 2500/40* (2013.01); *C12N 2510/00* (2013.01)

(58) Field of Classification Search
None
See application file for complete search history.

(56) References Cited

U.S. PATENT DOCUMENTS

| | | |
|---|---|---|
| 6,537,782 B1 | 3/2003 | Shibuya et al. |
| 2011/0104754 A1* | 5/2011 | Bramke ............... C12N 5/0018 435/69.1 |
| 2015/0105343 A1* | 4/2015 | Byrne ..................... A61P 17/00 514/52 |

FOREIGN PATENT DOCUMENTS

| | | |
|---|---|---|
| EP | 1818392 A1 | 8/2007 |
| EP | 1818392 B1 | 8/2010 |
| EP | 2351833 A1 | 8/2011 |
| JP | 2004-033227 A | 2/2004 |
| JP | 3950834 B2 | 4/2007 |
| WO | WO 2010/036767 A1 | 4/2010 |
| WO | WO 2015/057997 A1 | 4/2015 |

OTHER PUBLICATIONS

Supplementary European Search Report dated Sep. 28, 2018 in EP 16800098.2.
International Search Report dated Aug. 23, 2016, in PCT/JP2016/065625.
Chen et al., "Biphasic addition strategy of hypoxanthine and thymidine for improving monoclonal antibody production," Journal of Bioscience and Bioengineering, 2012, 114(3):347-352.
Gramer et al., "Modulation of Antibody Galactosylation Through Feeding of Uridine, Manganese Chloride, and Galactose," Biotechnology and Bioengineering, Jul. 2011, 108(7):1591-1602.
Huang et al., "Maximizing Productivity of CHO Cell-Based Fed-Batch Culture Using Chemically Defined Media Conditions and Typical Manufacturing Equipment," Biotechnol. Prog., 2010, 26(5):1400-1410.
Kochanowski et al., "Influence of Intracellular Nucleotide and Nucleotide Sugar Contents on Recombinant Interferon-γ Glycosylation During Batch and Fed-Batch Cultures of CHO Cells," Biotechnology and Bioengineering, Jul. 1, 2008, 100(4):721-733.
Wong et al., "An Investigation of Intracellular Glycosylation Activities in CHO Cells: Effects of Nucleotide Sugar Precursor Feeding," Biotechnology and Bioengineering, Oct. 1, 2010, 107(2):321-336.
Jayme et al., "Culture Media for Propagation of Mammalian Cells, Viruses, and Other Biologicals," Advances in Biotechnological Processes, Jan. 1, 1985, 5:1-30.

* cited by examiner

*Primary Examiner* — James D Schultz
(74) *Attorney, Agent, or Firm* — Foley & Lardner LLP

(57) ABSTRACT

An object of the present invention is to provide an animal cell culture method which is high in protein productivity.

Provided is a method for culturing animal cells in a culture medium, wherein the culture medium comprises a nucleic acid component(s) (deoxyuridine, thymidine, and/or deoxycytidine, or a salt(s) thereof). Also provided is a method for producing a protein, the method comprising the step of culturing animal cells expressing the protein in a culture medium, wherein the culture medium comprises a nucleic acid component(s).

2 Claims, 8 Drawing Sheets

CELL CULTURING METHOD USING NUCLEIC ACID-CONTAINING MEDIUM

CROSS-REFERENCE TO RELATED APPLICATIONS

This application is a National Stage application of PCT/JP2016/065625, filed May 26, 2016, which claims priority from Japanese application JP 2015-107147, filed May 27, 2015.

TECHNICAL FIELD

The present invention relates to a method for culturing cells producing a desired protein to thereby prepare said protein, and a method for preparing said protein using said culture method. More particularly, this invention relates to a method for culturing cells producing a desired protein to thereby prepare said protein, the method characterized in that adding nucleic acid components (deoxyuridine, thymidine, deoxycytidine, or a salt(s) thereof) to a culture medium enables promotion of cell growth, maintenance of cell viability rate, and enhancement of protein productivity.

BACKGROUND ART

In the process of culturing cells producing a desired protein to thereby prepare said protein, it was a challenge how to enhance protein productivity. For the purpose of solving this challenge, various techniques have been studied to perform cell engineering of host cells, to improve an expression vector, or to develop a new cell culture medium or method (NPL 1). Development of a culture medium is one solution to enhance protein productivity. In recent years, as understanding has grown about the nutritional requirements and metabolisms of cells, studies have been made to optimize the constitution and its concentration of culture media such as feed culture media (NPL 2). With regard to nucleic acid components used in the development of culture media, it has been reported that adding thymidine (0.2-7 mg/L) and uridine (5-10 mg/L) to a culture medium enables enhancement of cell growth and cell viability (PTL 1). However, for the purpose of protein production by animal cells, it is hard to say that these components and/or their concentrations are sufficient to obtain adequate protein production.

With regard to the nucleic acid component uridine, there was a report on the investigation of the effects of uridine feeding on the quality of a protein product (NPL 3), but no suggestion is made therein as to the improvement of protein production.

CITATION LIST

Patent Literature

PTL 1: European Patent No. EP 1818392

Non Patent Literatures

NPL 1: *Cell Culture Technology for Pharmaceutical and Cell-Based Therapies*, edited by Sadettin S. Ozturk and Wei-Shou Hu, U.S., CRC Press, 30 Aug. 2005
NPL 2: *Biotechnology Progress* 26: 1400-1410, 2010
NPL 3: *Biotechnology and Bioengineering* 107(2): 321-336, 2010

SUMMARY OF INVENTION

Technical Problem

An object of the present invention is to provide an animal cell culture method which is high in protein productivity.

Solution to Problem

In order to achieve the foregoing object, the present inventors have conducted considerable ingenious studies on culture media for animal cells. As a result, the inventors found that in the process of performing an animal cell culture method, adding a nucleic acid component(s) (deoxyuridine, thymidine, and/or deoxycytidine, or a salt(s) thereof) to a culture medium produces advantageous effects, which are promotion of cell growth, maintenance of cell viability, and enhancement of the protein productivity of animal cells. The present invention has been completed on the basis of this finding.

More specifically, the present invention includes the following.

(1) A method for culturing animal cells in a culture medium, wherein the culture medium comprises not less than 5 mg/L and not more than 500 mg/L of deoxyuridine or a salt thereof.
(2) The method as set forth in (1), wherein the culture medium comprises not less than 5 mg/L and not more than 200 mg/L of deoxyuridine or a salt thereof.
(3) The method as set forth in (1), wherein the culture medium comprises not less than 15 mg/L and not more than 100 mg/L of deoxyuridine or a salt thereof.
(4) The method as set forth in any of (1) to (3), wherein the culture medium further comprises not less than 15 mg/L and not more than 50 mg/L of thymidine or a salt thereof.
(5) The method as set forth in any of (1) to (3), wherein the culture medium further comprises not less than 15 mg/L and not more than 50 mg/L of deoxycytidine or a salt thereof.
(6) The method as set forth in (3), wherein the culture medium comprises not less than 15 mg/L and not more than 100 mg/L of deoxyuridine or a salt thereof, not less than 15 mg/L and not more than 50 mg/L of thymidine or a salt thereof, and not less than 15 mg/L and not more than 50 mg/L of deoxycytidine or a salt thereof.
(7) The method as set forth in any of (1) to (3), wherein the animal cells are cells having introduced therein a protein-coding gene.
(8) The method as set forth in (7), wherein the protein is an antibody.
(9) The method as set forth in (7), wherein the animal cells are Chinese hamster ovary (CHO) cells.
(10) A method for producing a protein, the method comprising the step of culturing animal cells expressing the protein in a culture medium, wherein the culture medium comprises not less than 10 mg/L and not more than 200 mg/L of deoxyuridine or a salt thereof.
(11) The method as set forth in (10), wherein the culture medium comprises not less than 15 mg/L and not more than 100 mg/L of deoxyuridine or a salt thereof.
(12) The method as set forth in (10) or (11), wherein the culture medium further comprises not less than 15 mg/L and not more than 50 mg/L of thymidine or a salt thereof.
(13) The method as set forth in (10) or (11), wherein the culture medium further comprises not less than 15 mg/L and not more than 50 mg/L of deoxycytidine or a salt thereof.

(14) The method as set forth in (11), wherein the culture medium comprises not less than 15 mg/L and not more than 100 mg/L of deoxyuridine or a salt thereof, not less than 15 mg/L and not more than 50 mg/L of thymidine or a salt thereof, and not less than 15 mg/L and not more than 50 mg/L of deoxycytidine or a salt thereof.

(15) The method as set forth in (10) or (11), wherein the animal cells are cells having introduced therein a protein-coding gene.

(16) The method as set forth in (15), wherein the protein is an antibody.

(17) The method as set forth in (15), wherein the animal cells are Chinese hamster ovary (CHO) cells.

Advantageous Effects of Invention

The methods of the present invention, which are a method for culturing animal cells and a method for producing a protein, produce advantageous effects, which are promotion of cell growth, maintenance of cell viability, and enhancement of the protein productivity of animal cells.

DESCRIPTION OF EMBODIMENTS

Figure 1:
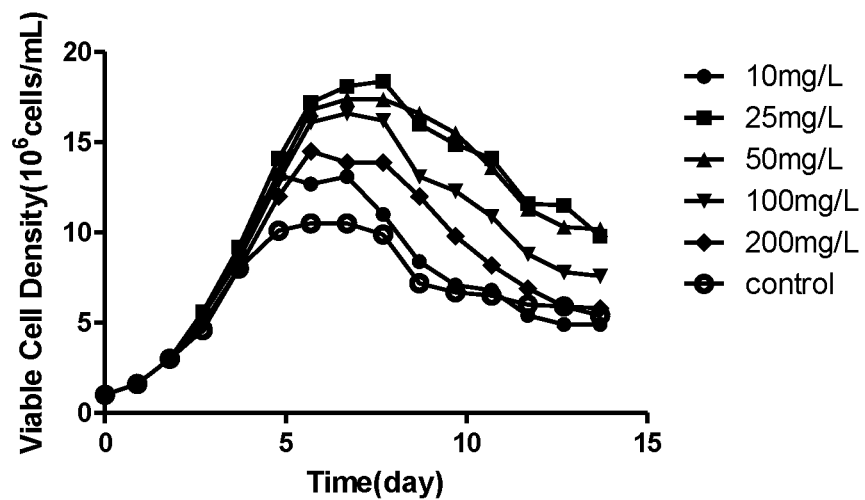
FIG. 1 shows the effects of deoxyuridine addition on change in viable cell density during the culture period. The vertical axis represents viable cell density ($\times 10^6$ cells/mL), and the horizontal axis represents culture period (days).

Hereunder, the present invention will be specifically described, but this invention is not limited by the specific descriptions provided below.

Unless otherwise defined herein, all scientific and technical terms used in relation to the present invention shall have meanings commonly understood by those skilled in the art.

The present invention relates to a method for culturing animal cells in a culture medium comprising a nucleic acid component, and to a method for producing a protein, the method comprising the step of culturing animal cells expressing the protein in a culture medium comprising a nucleic acid component.

Nucleic Acid Component(s)

As referred to herein, the "nucleic acid component(s)" refers to one or more substances selected from the group consisting of deoxyuridine (dU), thymidine (dT) and deoxycytidine (dC), or salts thereof.

The culture medium used in the methods of the present invention comprises deoxyuridine or a salt thereof. Preferably, the culture medium used in the methods of this invention further comprises thymidine and/or deoxycytidine, or a salt(s) thereof.

Examples of the salts of deoxyuridine, thymidine, and deoxycytidine include, but are not particularly limited to, metallic salts such as sodium salt, inorganic salts such as ammonium salt, hydrohalogenic acid salts such as hydrochloride, inorganic acid salts, and organic acid salts. A preferred example of said salts is hydrochloride.

Culturing animal cells in a culture medium having added thereto deoxyuridine or a salt thereof produces various effects on the cultured animal cells, which are promotion of cell growth and enhancement of protein productivity.

Culturing animal cells in a culture medium having added thereto deoxyuridine, thymidine, and deoxycytidine, or salts thereof produces various effects on the cultured animal cells, which are promotion of cell growth, maintenance or improvement of cell viability, and enhancement of protein productivity. It was confirmed that, as compared to addition of deoxyuridine or thymidine alone, addition of all three of deoxyuridine, thymidine, and deoxycytidine creates a synergistic effect.

Deoxyuridine or a salt thereof is present in a culture medium at a concentration of, for example, not less than 5 mg/L and not more than 500 mg/L, preferably not less than 5 mg/L and not more than 200 mg/L, not less than 10 mg/L and not more than 500 mg/L, not less than 10 mg/L and not more than 200 mg/L, not less than 15 mg/L and not more than 100 mg/L, not less than 20 mg/L and not more than 100 mg/L, not less than 25 mg/L and not more than 100 mg/L, not less than 15 mg/L and not more than 85 mg/L, not less than 20 mg/L and not more than 85 mg/L, or not less than 25 mg/L and not more than 85 mg/L.

Thymidine or a salt thereof is present in a culture medium at a concentration of, for example, not less than 15 mg/L and not more than 50 mg/L, preferably not less than 20 mg/L and not more than 50 mg/L, or not less than 25 mg/L and not more than 50 mg/L.

Deoxycytidine or a salt thereof is present in a culture medium at a concentration of, for example, not less than 15 mg/L and not more than 50 mg/L, preferably not less than 20 mg/L and not more than 50 mg/L, or not less than 25 mg/L and not more than 50 mg/L.

Culture Medium

The culture medium used in the methods of the present invention is not particularly limited as long as the culture medium is capable of proliferating animal cells and comprises the nucleic acid component(s) as described above. One skilled in the art can select an appropriate culture medium depending on the type of the cells to be cultured. For example, there can be used a culture medium prepared by adding the aforementioned nucleic acid component(s) to a culture medium selected from the group consisting of CD CHO Medium (Life Technologies), CD OptiCHO Medium (Life Technologies), DMEM (Life Technologies), EX-CELL® 302 (Sigma), and BD Select CD1000 (BD Bioscience).

Animal Cells

The animal cells cultured in the methods of the present invention are not particularly limited. Examples of the animal cells include Chinese hamster ovary (CHO) cells, hybridoma cells, human embryonic kidney (HEK293) cells, murine myeloma (Sp2/0 or NS0) cells, baby hamster kidney (BHK) cells, and African green monkey kidney (COS) cells.

In a preferred embodiment, the animal cells are animal cells expressing a desired protein. The protein-expressing animal cells can be wild-type cells expressing a desired protein, or can be cells having introduced therein a gene encoding a desired protein.

The cells having introduced therein a protein-coding gene are recombinant cells transfected with an expression vector that permits expression of a protein-coding gene in cells. The expression vector can be a DNA vector or an RNA vector, and typically can be a plasmid vector or a viral vector.

The protein to be expressed by the animal cells can be selected by one skilled in the art as appropriate. In a preferred embodiment, the protein is an antibody.

Method for Culturing Animal Cells

The present invention provides a method for culturing animal cells. Said culture method comprises the step of culturing animal cells in a culture medium comprising nucleic acid components.

The type(s) and amount(s) added of the nucleic acid components to be adopted in specific embodiments are as described above in the section titled "Nucleic acid components". Also, the culture medium to be used and the animal cells to be cultured are as described above in the sections titled "Culture medium" and "Animal cells", respectively.

The culture conditions can be selected by one skilled in the art as appropriate depending on the type of the animal cells. For example, CHO cells are preferably cultured under the conditions of 36.5° C. and 5% $CO_2$.

The culture mode can be selected by one skilled in the art as appropriate depending on the type of the animal cells and the culture conditions. For example, different culture modes used for seed culture and production culture can be adopted, such as fed-batch culture, batch culture, perfusion culture and continuous culture.

The culture system is not particularly limited, and cell culture can be performed in various culture systems such as stirred-tank bioreactor system and hollow fiber bioreactor system.

The culture scale is not particularly limited, and cell culture can be performed on different culture scales such as flask, benchtop bioreactor and tank bioreactor scales.

The timing and frequency of adding a nucleic acid component(s) to a culture medium are not particularly limited. As for the timing of adding a nucleic acid component(s) to a culture medium, addition can be done, for example, at the start of culture or after the start of culture. In the case of adding a nucleic acid component(s) to a culture medium after the start of culture, addition can be done, for example, after 1 hour, 5 hours, 10 hours, 15 hours, 24 hours (1 day), 36 hours, 48 hours (2 days), 3 days, 4 days, or 5 days from the start of culture. As for the frequency of adding nucleic acid components, addition can be done, for example, just once, or several times (e.g., 2, 3, 4, 5 times) in divided doses.

Culturing animal cells in a culture medium comprising nucleic acid component(s) produces various effects, which are promotion of cell growth and/or maintenance of cell viability, or enhancement of protein productivity in the case of using animal cells expressing a protein. The relationship of the specific type(s) of the nucleic acid components to be added with the observed effects is as described above in the section titled "Nucleic acid components".

Method for Producing a Protein

The present invention provides a method for producing a protein by culturing animal cells expressing the protein. Said method comprises the step of culturing animal cells expressing a protein in a culture medium comprising nucleic acid components. The type(s) and amount(s) added of the nucleic acid components are as described above in the section titled "Nucleic acid components". Also, the culture medium to be used and the animal cells to be cultured are as described above in the sections titled "Culture medium" and "Animal cells", respectively. Further, the culture conditions, culture mode, culture scale, and the timing and frequency of adding nucleic acid components to a culture medium are as described above in the section titled "Method for culturing animal cells".

The method for producing a protein not only comprises the step of culturing animal cells expressing a protein in a culture medium comprising nucleic acid components, but also may further comprise the step of recovering the protein produced by culturing animal cells. Protein recovery can be done by one skilled in the art as appropriate depending on the properties of the expressed protein. Various types of chromatography, such as gel filtration chromatography, ion exchange chromatography, and affinity chromatography, can be used for this purpose. For example, when the protein is an antibody, affinity chromatography with a protein A- or protein G-bound carrier can be used to recover the antibody.

Culturing animal cells expressing a protein in a culture medium comprising nucleic acid components produces various effects, which are promotion of cell growth, maintenance of cell viability, and/or enhancement of protein productivity. The relationship of the specific type(s) of the nucleic acid components to be added with the observed effects is as described above in the section titled "Nucleic acid components".

EXAMPLES

Hereunder, the present invention will be specifically described by way of working examples. However, these working examples are intended to illustrate this invention and not to limit the scope of this invention.

Example 1

Effects of Deoxyuridine Addition in Fed-Batch Culture

Figure 2:
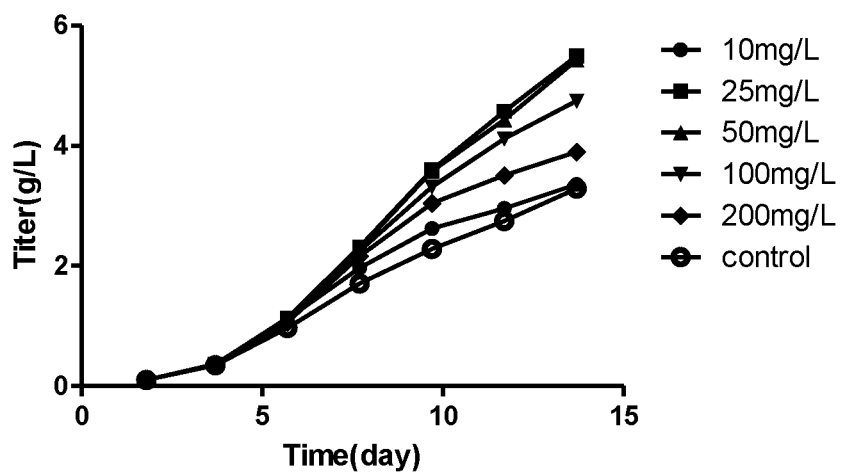
FIG. 2 shows the effects of deoxyuridine addition on change in produced antibody concentration during the culture period. The vertical axis represents produced antibody titer (g/L), and the horizontal axis represents culture period (days).

Using a culture medium for animal cells as a cell growth medium, fed-batch culture of an IgG-expressing CHO cell line (a CHO cell line in which an anti-human thymic stromal lymphopoietin (TSLP) receptor antibody (fully human T7-27) had been recombinantly expressed, as described in WO 2015/020193) was started at an initial viable cell density of $1 \times 10^6$ cells/mL under the conditions of 36.5° C. and 5% $CO_2$. On day 2 of culture, deoxyuridine was added to cultures to a final concentration of 10, 25, 50, 100 or 200 mg/L. The culture was continued until day 14 of culture while a feed medium was added everyday from day 2 of culture. Sampling was done at appropriate timings. Viable cell densities were measured by trypan blue exclusion study, and antibody concentrations were measured by protein A column HPLC. As shown in FIGS. 1 and 2, in the case of no addition of deoxyuridine (control), the highest viable cell density observed during the 14 days of culture was about $10 \times 10^6$ cells/mL, and the antibody concentration on the final day of culture was 3.3 g/L. In contrast, in the case of addition of 25 mg/L deoxyuridine, the highest viable cell density observed during the 14 days of culture was about $18 \times 10^6$ cells/mL, and the antibody concentration on the final day of culture was 5.5 g/L; these values were higher than control. The results suggested that deoxyuridine is capable of enhancing cell proliferation and antibody production. Further, in all the cases of adding deoxyuridine at any of the concentrations tested from 10 mg/L to 200 mg/L, the cells showed responses to deoxyuridine addition; they were observed to exhibit enhanced cell growth and antibody production. It was also observed that even addition of 10 mg/mL deoxyuridine enhancedantibody production during the cell culture until day 10 to day 12.

Example 2

Figure 3:
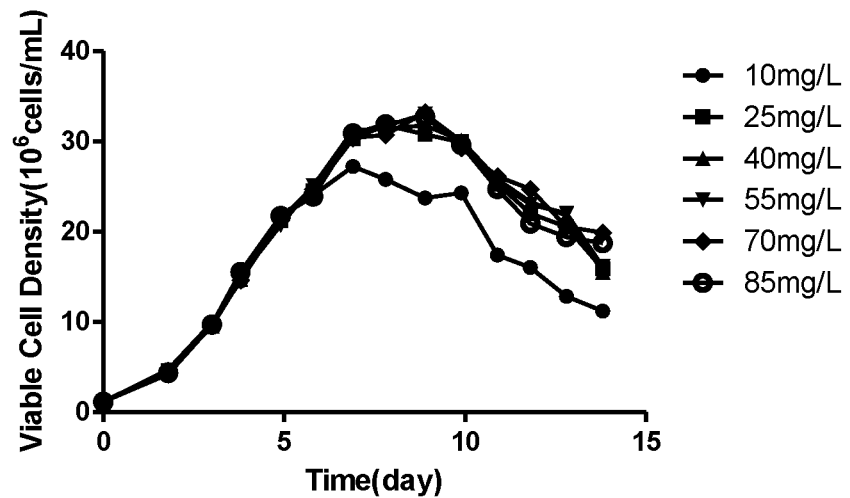
FIG. 3 shows the effects of addition of deoxyuridine (10-85 mg/L) in the presence of thymidine (25 mg/L) and deoxycytidine (25 mg/L) on change in viable cell density during the culture period. The vertical axis represents viable cell density ($\times 10^6$ cells/mL), and the horizontal axis represents culture period (days).
Figure 4:
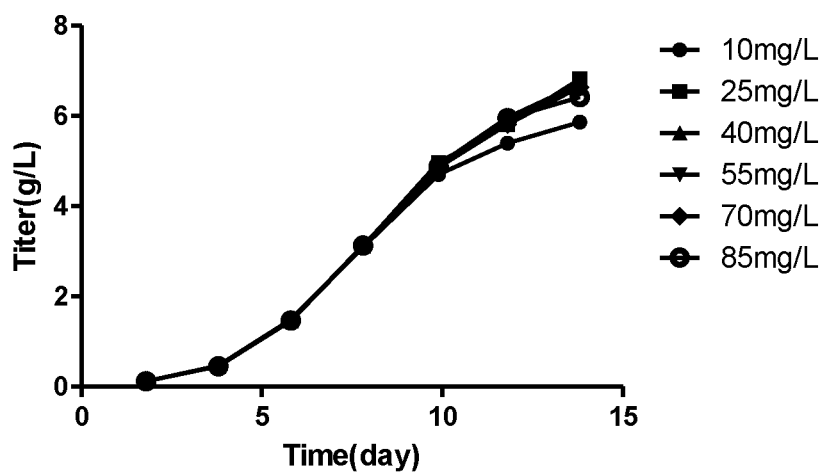
FIG. 4 shows the effects of addition of deoxyuridine (10-85 mg/L) in the presence of thymidine (25 mg/L) and deoxycytidine (25 mg/L) on change in produced antibody concentration during the culture period. The vertical axis represents produced antibody titer (g/L), and the horizontal axis represents culture period (days).

Detailed Concentrations of Deoxyuridine Added in the Presence of Thymidine and Deoxycytidine, and the Effects of Such Additions, in Fed-Batch Culture Using a culture medium for animal cells as a cell growth medium, fed-batch culture of an IgG-expressing CHO cell line (a CHO cell line in which an anti-human TSLP receptor antibody (fully human T7-27) had been recombinantly expressed, as described in WO 2015/020193) was started at an initial viable cell density of $1 \times 10^6$ cells/mL under the conditions of 36.5° C. and 5% $CO_2$. At the start of culture, thymidine and deoxycytidine hydrochloride (in the working examples given in the subject specification, deoxycytidine hydrochloride was actually used as deoxycytidine, and the concentrations of deoxycytidine hydrochloride are expressed by using the converted concentration value of deoxycytidine from deoxycytidine hydrochloride.) were each added to cultures to a final concentration of 25 mg/L, and deoxyuridine was added to a final concentration of 10, 25, 40, 55, 70 or 85 mg/L. The culture was continued until day 14 of culture while a feed culture medium was added everyday from day 2 of culture. Sampling was done at appropriate timings. Viable cell densities were measured by trypan blue exclusion method, and antibody concentrations were measured by protein A column HPLC. As shown in FIGS. 3 and 4, in the case of addition of 10 mg/L of deoxyuridine, the highest viable cell density observed during the 14 days of culture was about $27 \times 10^6$ cells/mL, and the antibody concentration on the final day of culture was 5.9 g/L. In contrast, in the case of addition of 25 mg/L deoxyuridine, the highest viable cell density observed during the 14 days of culture was approximately $32 \times 10^6$ cells/mL, and the antibody concentration on the final day of culture was 6.8 g/L; these values were higher than in the case of addition of 10 mg/L of deoxyuridine. The results suggested that in the presence of thymidine and deoxycytidine, the addition of deoxyuridine at concentrations of 25 mg/L or higher produces higher enhancing effects on cell growth and antibody production than the addition of 10 mg/L of deoxyuridine.

Example 3

Figure 5:
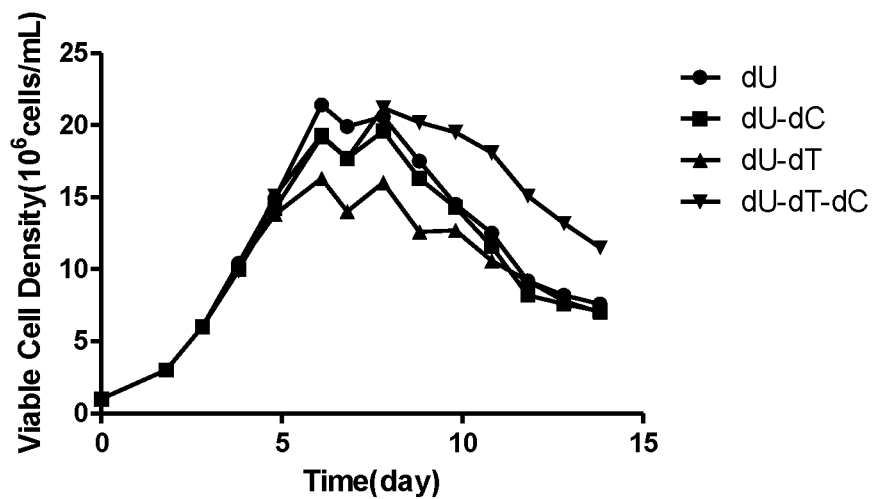
FIG. 5 shows the effects of addition of deoxyuridine, thymidine or deoxycytidine alone, or any combination of them on change in viable cell density during the culture period. The vertical axis represents viable cell density ($\times 10^6$ cells/mL), and the horizontal axis represents culture period (days).
Figure 6:
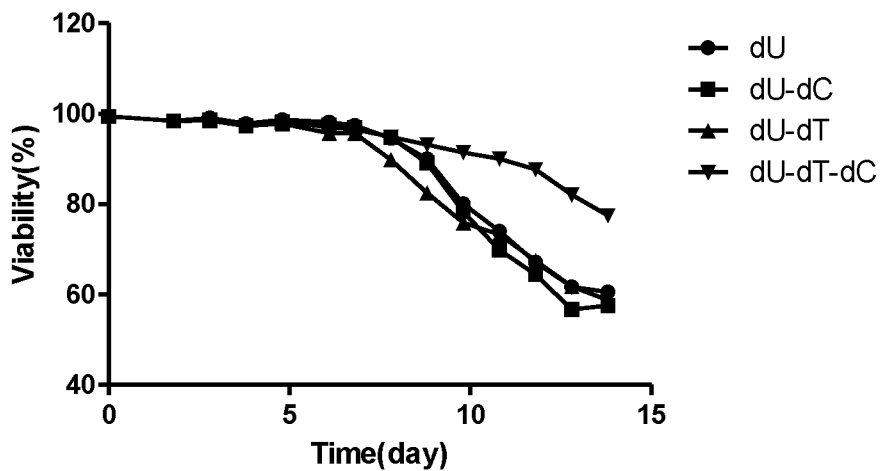
FIG. 6 shows the effects of addition of deoxyuridine, thymidine or deoxycytidine alone, or any combination of them on change in cell viability during the culture period. The vertical axis represents cell viability (%), and the horizontal axis represents culture period (days).
Figure 7:
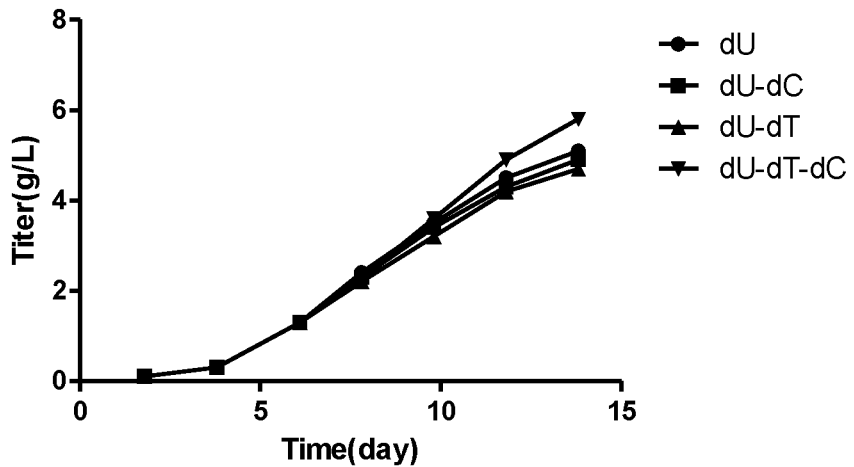
FIG. 7 shows the effects of addition of deoxyuridine, thymidine or deoxycytidine alone, or any combination of them on change in produced antibody concentration during the culture period. The vertical axis represents produced antibody titer (g/L), and the horizontal axis represents culture period (days).

Effects of Addition of Deoxyuridine, Thymidine and Deoxycytidine in Fed-Batch Culture Using a culture medium for animal cells as a cell growth medium, fed-batch culture of an IgG-expressing CHO cell line (a CHO cell line in which an anti-human TSLP receptor antibody (fully human T7-27) had been recombinantly expressed, as described in WO 2015/020193) was started at an initial viable cell density of $1 \times 10^6$ cells/mL under the conditions of 36.5° C. and 5% $CO_2$. On day 2 of culture, deoxyuridine was added to a final concentration of 25 mg/L, and thymidine and deoxycytidine were each added to cultures to a final concentration of 0 or 25 mg/L according to Table 1. The culture was continued until day 14 of culture while a feed culture medium was added everyday from day 2 of culture. Sampling was done at appropriate timings. Viable cell densities were measured by trypan blue exclusion method, and antibody concentrations were measured by protein A column HPLC. As shown in FIGS. 5, 6 and 7, in the case of addition of deoxyuridine alone in the absence of thymidine and deoxycytidine (dU), the viable cell density, cell viability, and antibody concentration on the final day of the 14 days of culture were approximately $7.6 \times 10^6$ cells/mL, approximately 61%, and 5.1 g/L, respectively. In contrast, in the case of addition of deoxyuridine in the presence of 25 mg/L each of thymidine and deoxycytidine (dU-dT-dC), the viable cell density, cell viability, and antibody concentration on the final day of the 14 days of culture were $12 \times 10^6$ cells/mL, approximately 78%, and 5.8 g/L, respectively; these values were higher than in the cases of addition of dU, addition of deoxyuridine and deoxycytidine (dU-dC), and addition of deoxyuridine and thymidine (dU-dT). The results suggested that addition of both thymidine and deoxycytidine in the presence of deoxyuridine enables maintenance of cell viability and produces an enhancing effect on antibody production.

TABLE 1

Nucleic acid concentrations in each experimental condition.

| Legend | Deoxyuridine (dU) | Thymidine (dT) | Deoxycytidine (dC) |
| --- | --- | --- | --- |
| dU | 25 mg/L | 0 mg/L | 0 mg/L |
| dU-dC | 25 mg/L | 0 mg/L | 25 mg/L |
| dU-dT | 25 mg/L | 25 mg/L | 0 mg/L |
| dU-dT-dC | 25 mg/L | 25 mg/L | 25 mg/L |

Example 4

Figure 8:
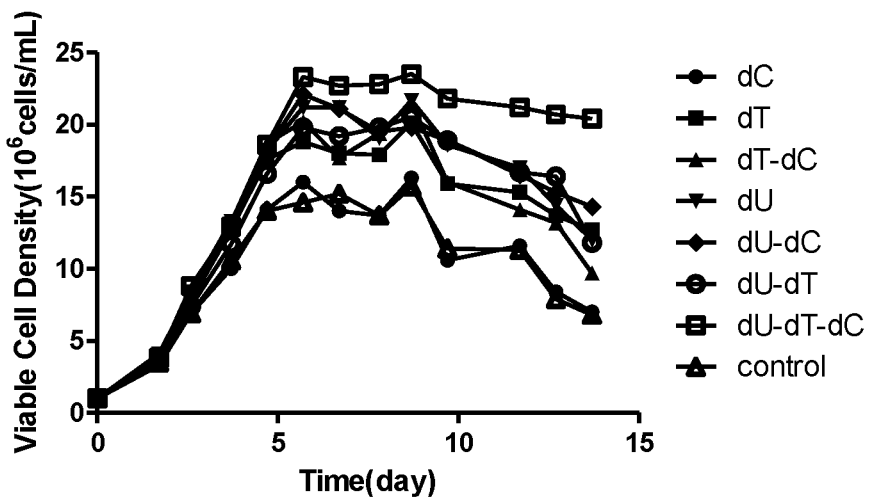
FIG. 8 shows the effects of addition of deoxyuridine, thymidine or deoxycytidine alone, or any combination of them on change in viable cell density during the culture period. The vertical axis represents viable cell density ($\times 10^6$ cells/mL), and the horizontal axis represents culture period (days).
Figure 9:
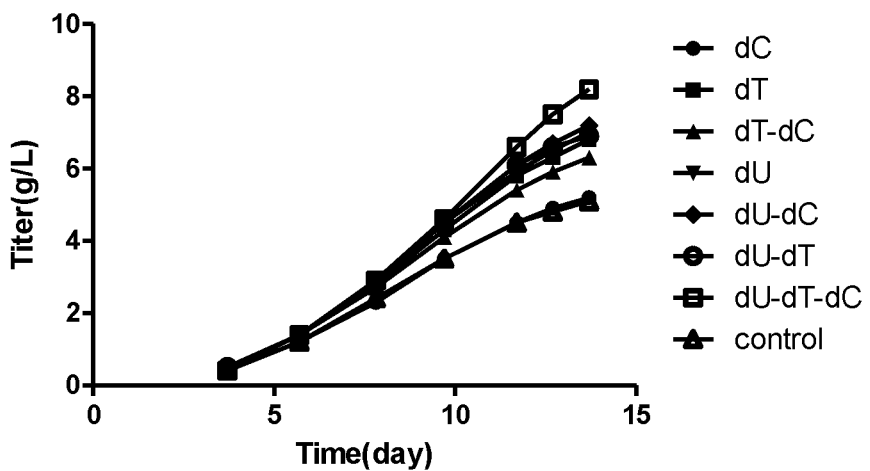
FIG. 9 shows the effects of addition of deoxyuridine, thymidine or deoxycytidine alone, or any combination of them on change in produced antibody concentration during the culture period. The vertical axis represents produced antibody titer (g/L), and the horizontal axis represents culture period (days).

Effects of Addition of Deoxyuridine, Thymidine and Deoxycytidine in Fed-Batch Culture Using a culture medium for animal cells as a cell growth medium, fed-batch culture of an IgG-expressing CHO cell line (a CHO cell line in which an anti-human α9 antibody (RY9A2v12 (M34L) 012) had been recombinantly expressed, as described in WO 2009/088064) was started at an initial viable cell density of $1 \times 10^6$ cells/mL under the conditions of 36.5° C. and 5% $CO_2$. At the start of culture, deoxyuridine, thymidine, and/or deoxycytidine was/were each added to a final concentration of 0 or 25 mg/L according to Table 2. The culture was continued until day 14 of culture while a feed culture medium was added everyday from day 2 of culture. Sampling was done at appropriate timings. Viable cell densities were measured by trypan blue exclusion method, and antibody concentrations were measured by protein A column HPLC. As shown in FIGS. 8 and 9, in the case of no addition of a nucleic acid component (deoxyuridine, thymidine or deoxycytidine) (control), the highest viable cell density observed during the 14 days of culture was approximately $16 \times 10^6$ cells/mL, and the antibody concentration on the final day of culture was 5.1 g/L. In contrast, in the case of addition of deoxyuridine, thymidine, and deoxycytidine, each at a concentration of 25 mg/L (dU-dT-dC), the highest viable cell density observed during the 14 days of culture was approximately $23 \times 10^6$ cells/mL, and the antibody concentration on the final day of culture was 8.2 g/L; these values were higher than control.

Deoxyuridine and thymidine were each observed to produce effects when added alone, but no effect was observed in the case of addition of deoxycytidine alone. Meanwhile, although thymidine was observed to produce effects when added alone, no synergic effect was found in the case of addition of thymidine in combination with deoxyuridine or deoxycytidine. However, addition of all three of deoxyuridine, thymidine and deoxycytidine was found to exert a synergic effect and was suggested to produce the highest effects.

TABLE 2

Nucleic acid concentrations in each experimental condition.

| Legend | Deoxyuridine (dU) | Thymidine (dT) | Deoxycytidine (dC) |
| --- | --- | --- | --- |
| control | 0 mg/L | 0 mg/L | 0 mg/L |
| dC | 0 mg/L | 0 mg/L | 25 mg/L |
| dT | 0 mg/L | 25 mg/L | 0 mg/L |
| dT-dC | 0 mg/L | 25 mg/L | 25 mg/L |
| dU | 25 mg/L | 0 mg/L | 0 mg/L |
| dU-dC | 25 mg/L | 0 mg/L | 25 mg/L |
| dU-dT | 25 mg/L | 25 mg/L | 0 mg/L |
| dU-dT-dC | 25 mg/L | 25 mg/L | 25 mg/L |

Example 5

Figure 10:
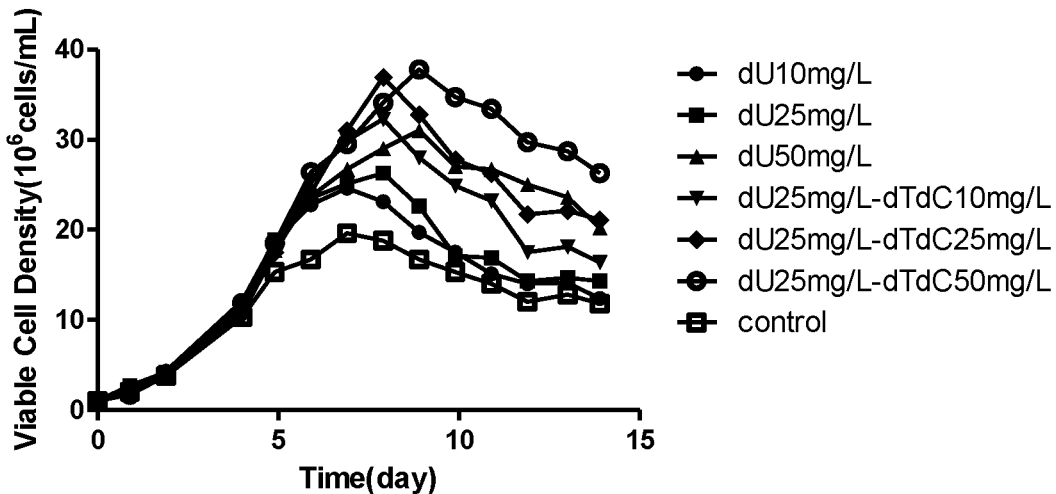
FIG. 10 shows the effects of addition of deoxyuridine, thymidine or deoxycytidine alone, or any combination of them on change in viable cell density during the culture period. The vertical axis represents viable cell density ($\times 10^6$ cells/mL), and the horizontal axis represents culture period (days).
Figure 11:
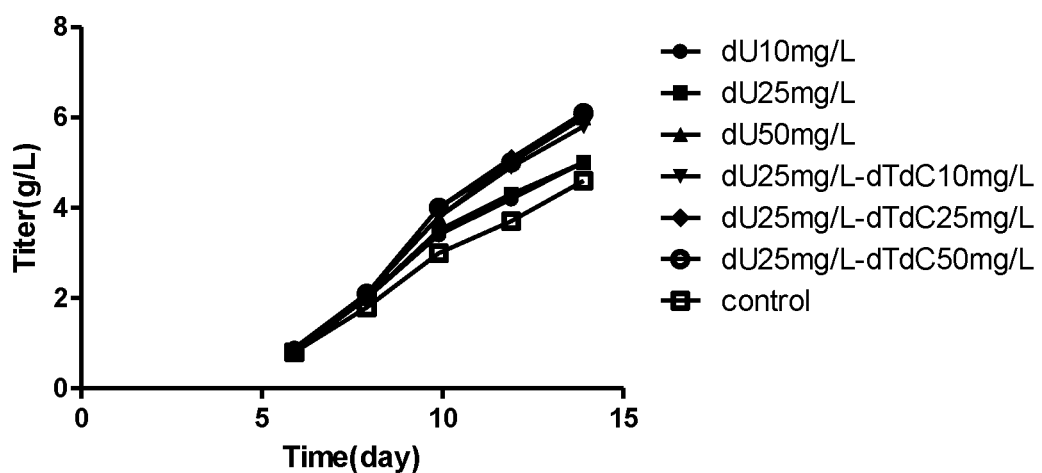
FIG. 11 shows the effects of addition of deoxyuridine, thymidine or deoxycytidine alone, or any combination of them on change in produced antibody concentration during the culture period. The vertical axis represents produced antibody titer (g/L), and the horizontal axis represents culture period (days).

Effects of Addition of Deoxyuridine, Thymidine and Deoxycytidine in Fed-Batch Culture Using a culture medium for animal cells as a cell growth medium, fed-batch culture of a Fab' fragment-expressing CHO cell line (a CHO cell line in which an anti-human NGF antibody Fab' fragment (1-15 (N52D-A)-Fab') had been expressed, as described in WO 2013/022083) was started at an initial viable cell density of $1 \times 10^6$ cells/mL under the conditions of 36.5° C. and 5% $CO_2$. At the start of culture, deoxyuridine, thymidine and deoxycytidine were each added to cultures to a final concentration of 0, 10, 25 or 50 mg/L according to Table 3. The culture was continued until day 14 of culture while a feed culture medium was added everyday from day 2 of culture. Sampling was done at appropriate timings. Viable cell densities were measured by trypan blue exclusion method, and antibody concentrations were measured by reverse-phase HPLC. As shown in FIGS. 10 and 11, in the case of no addition of a nucleic acid component (deoxyuridine, thymidine or deoxycytidine) (control), the highest viable cell density observed during the 14 days of culture was approximately 20×10⁶ cells/mL, and the protein concentration on the final day of culture was 4.6 g/L. In contrast, in the case of addition of 25 mg/L of deoxyuridine and 50 mg/L each of thymidine and deoxycytidine (dU25 mg/L-dTdC50 mg/L), the highest viable cell density observed during the 14 days of culture was approximately 38×10⁶ cells/mL, and the protein concentration on the final day of culture was 6.1 g/L; these values were higher than control. The results suggested that deoxyuridine is capable of enhancing cell growth and antibody production. It was also suggested that addition of both thymidine and deoxycytidine in the presence of deoxyuridine produces enhancing effects on cell growth and antibody production.

TABLE 3

Nucleic acid concentrations in each experimental condition

| Legend | Deoxyuridine (dU) | Thymidine (dT) | Deoxycytidine (dC) |
|---|---|---|---|
| control | 0 mg/L | 0 mg/L | 0 mg/L |
| dU10mg/L | 10 mg/L | 0 mg/L | 0 mg/L |
| dU25mg/L | 25 mg/L | 0 mg/L | 0 mg/L |
| dU50mg/L | 50 mg/L | 0 mg/L | 0 mg/L |
| dU25mg/L-dTdC10mg/L | 25 mg/L | 10 mg/L | 10 mg/L |
| dU25mg/L-dTdC25mg/L | 25 mg/L | 25 mg/L | 25 mg/L |
| dU25mg/L-dTdC50mg/L | 25 mg/L | 50 mg/L | 50 mg/L |

Example 6

Effects of Deoxyuridine Addition in Batch Culture

Figure 12:
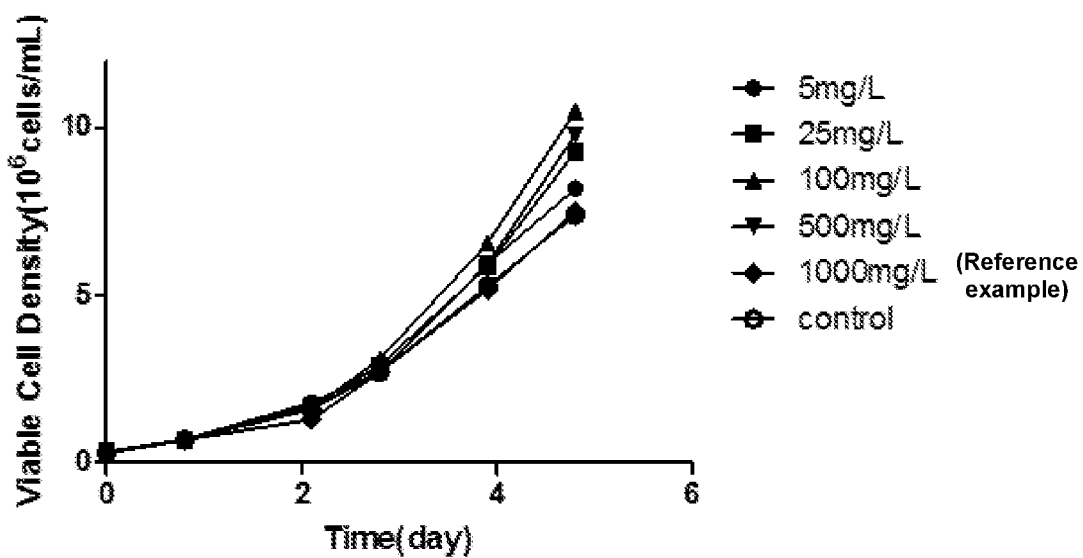
FIG. 12 shows the effects of deoxyuridine addition on change in viable cell density during the culture period. The vertical axis represents viable cell density ($\times 10^6$ cells/mL), and the horizontal axis represents culture period (days).

Using a culture medium for animal cells as a cell growth medium, batch culture of an IgG-expressing CHO cell line (a CHO cell line in which an anti-human α9 integrin antibody (hereinafter referred to as "anti-human α9 antibody") (RY9A2v12 (M34L) 012) had been recombinantly expressed, as described in WO 2009/088064) was started at an initial viable cell density of 0.3×10⁶ cells/mL under the conditions of 36.5° C. and 5% $CO_2$. At the start of culture, deoxyuridine was added to cultures to a final concentration of 5, 25, 100, 500 or 1000 mg/L, and then the culture was continued for 5 days. Sampling was done at appropriate timings. Viable cell densities were measured bytrypan blue exclusion method, and antibody concentrations were measured by protein A column HPLC. As shown in FIG. 12, in the case of no addition of deoxyuridine (control), the highest viable cell density observed during the 5 days of culture was approximately 7×10⁶ cells/mL, whereas in the case of addition of 100 mg/L of deoxyuridine, the highest viable cell density was approximately 10×10⁶ cells/mL, which was higher than control. It was also confirmed that addition of deoxyuridine at any of the concentrations tested from 5 mg/L to 500 mg/L produces an enhancing effect on cell growth.

Example 7

Figure 13:
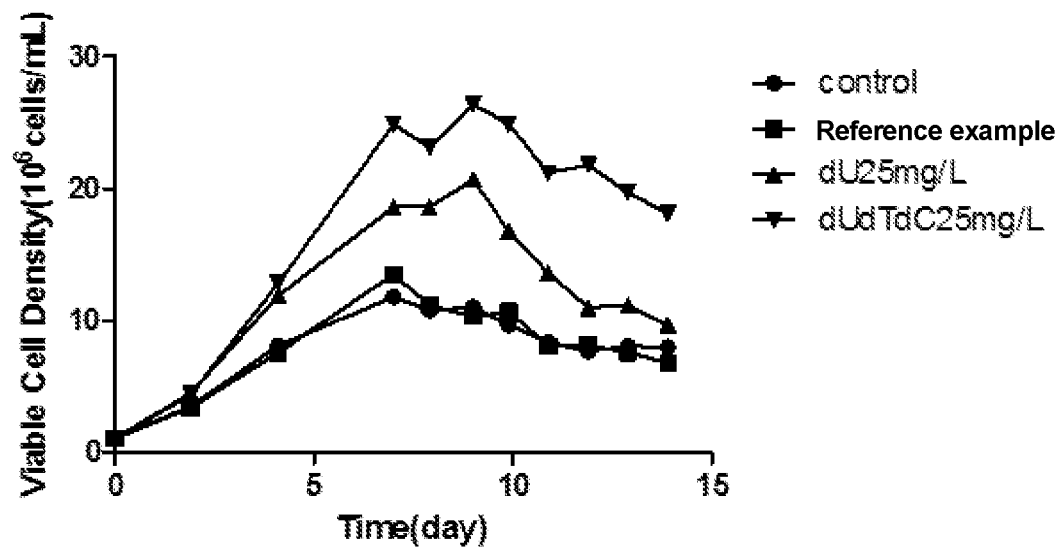
FIG. 13 shows the effects of addition of deoxyuridine, thymidine or deoxycytidine alone or any combination of them on change in viable cell density during the culture period, with those effects of addition of uridine and thymidine. The vertical axis represents viable cell density ($\times 10^6$ cells/mL), and the horizontal axis represents culture period (days).
Figure 14:
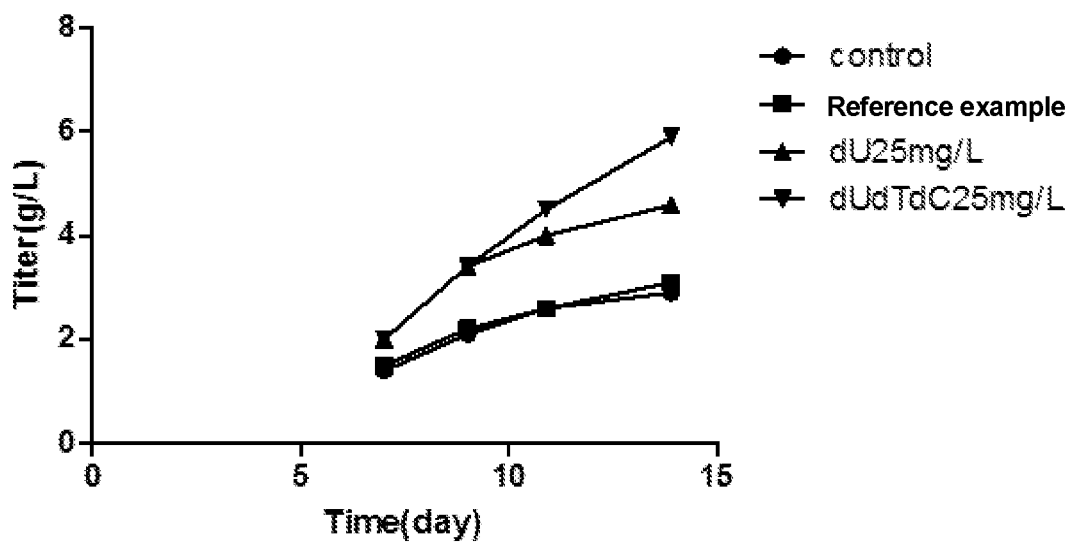
FIG. 14 shows the effects of addition of deoxyuridine, thymidine or deoxycytidine alone, or any combination of them on change in produced antibody concentration during the culture period, with those effects of addition of uridine and thymidine. The vertical axis represents produced antibody titer (g/L), and the horizontal axis represents culture period (days).

Effects of Addition of Deoxyuridine, Thymidine and Deoxycytidine in Fed-Batch Culture Using a culture medium for animal cells as a cell growth medium, fed-batch culture of an IgG-expressing CHO cell line (a CHO cell line in which an anti-human TSLP receptor antibody (fully human T7-27) had been recombinantly expressed, as described in WO 2015/020193) was started at an initial viable cell density of 1×10⁶ cells/mL under the conditions of 36.5° C. and 5% $CO_2$. At the start of culture, deoxyuridine, thymidine and deoxycytidine were each added to a final concentration of 25 mg/L. To provide comparative conditions, uridine (U) and thymidine were added, at the start of culture, at concentrations of 7 mg/L and 0.24 mg/L, respectively (these concentrations are the same as those described in Examples of EP 1818392 B1). The culture was continued under each of the different conditions described above until day 14 of culture while a feed culture medium was added everyday from day 2 of culture. Sampling was done at appropriate timings. Viable cell densities were measured by trypan blue exclusion method, and antibody concentrations were measured by protein A column HPLC. As shown in FIGS. 13 and 14, in the case of no addition of a nucleic acid component (deoxyuridine, thymidine or deoxycytidine) (control), the highest viable cell density observed during the 14 days of culture was approximately 12×10⁶ cells/mL, and the antibody concentration on the final day of culture was approximately 2.9 g/L. In contrast, in the case of addition of 25 mg/L of deoxyuridine (dU25 mg/L), the highest viable cell density observed during the 14 days of culture was approximately 21×10⁶ cells/mL, and the antibody concentration on the final day of culture was approximately 4.6 g/L; these values were higher than control. Further, in the case of addition of 25 mg/L each of deoxyuridine, thymidine and deoxycytidine (dUdTdC25 mg/L), the highest viable cell density observed during the 14 days of culture was approximately 26×10⁶ cells/mL, and the antibody concentration on the final day of culture was approximately 5.9 g/L; these values were much higher than control and dU25 mg/L. These results suggested that deoxyuridine is capable of enhancing cell proliferation and antibody production, and that addition of not only deoxyuridine but also thymidine and deoxycytidine produces further enhancing effects on cell growth and antibody production. It was also suggested that the enhancing effects of addition of the three components on cell growth and antibody production are superior to those of addition of 7 mg/L of uridine and 0.24 mg/L of thymidine (reference example).

Example 8

Figure 15:
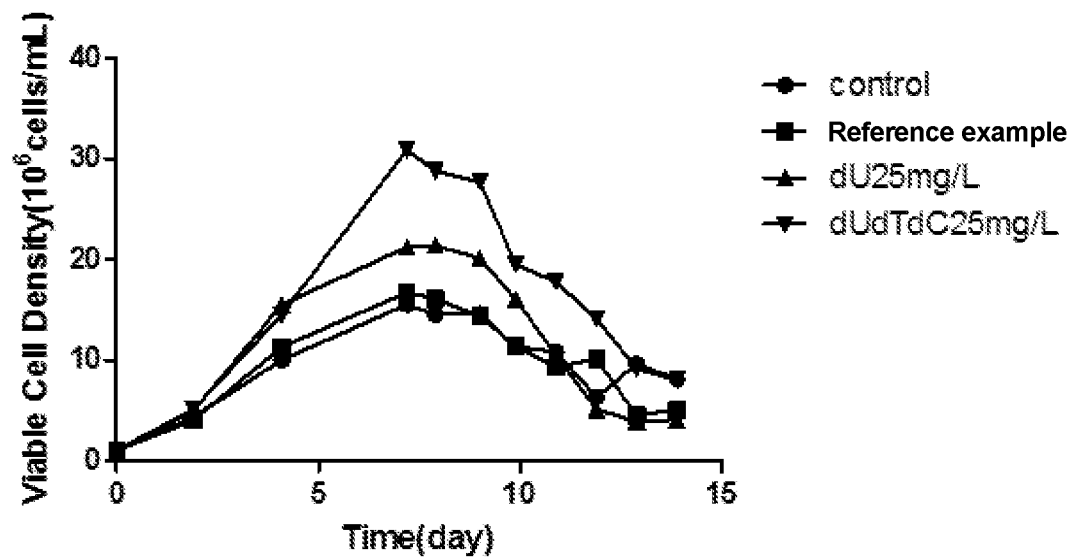
FIG. 15 shows the effects of addition of deoxyuridine, thymidine or deoxycytidine alone, or any combination of them on change in viable cell density during the culture period, with those effects of addition of uridine and thymidine. The vertical axis represents viable cell density ($\times 10^6$ cells/mL), and the horizontal axis represents culture period (days).
Figure 16:
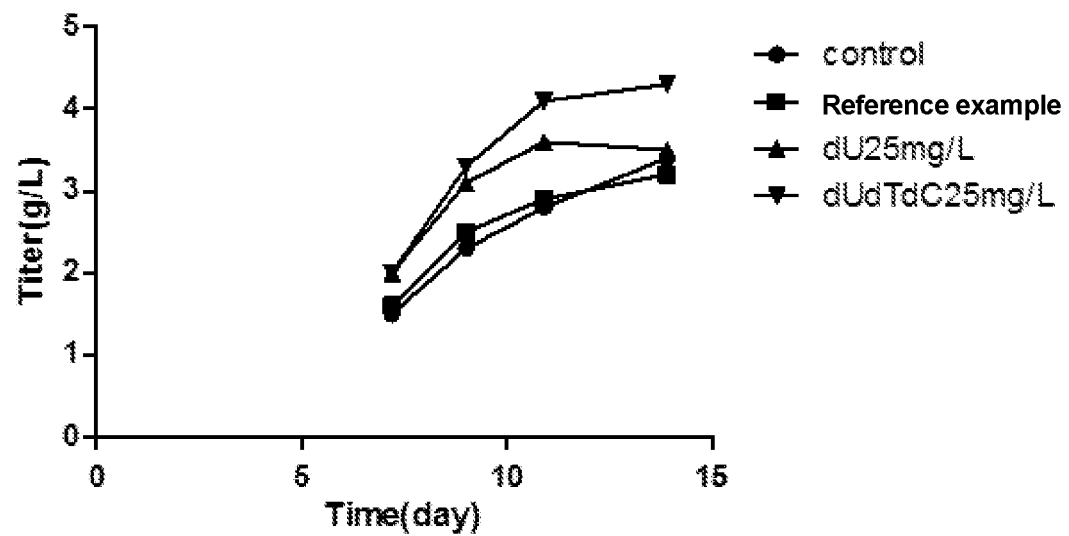
FIG. 16 shows the effects of addition of deoxyuridine, thymidine or deoxycytidine alone, or any combination of them on change in produced antibody concentration during the culture period, with those effects of addition of uridine and thymidine. The vertical axis represents produced antibody titer (g/L), and the horizontal axis represents culture period (days).

Effects of Addition of Deoxyuridine, Thymidine and Deoxycytidine in Fed-Batch Culture Using a culture medium for animal cells as a cell growth medium, fed-batch culture of an IgG-expressing CHO cell line (a CHO cell line in which an anti-human α9 antibody (RY9A2v12 (M34L) 012) had been recombinantly expressed, as described in WO 2009/088064) was started at an initial viable cell density of 1×10⁶ cells/mL under the conditions of 36.5° C. and 5% $CO_2$. At the start of culture, deoxyuridine, thymidine and deoxycytidine were each added to a final concentration of 25 mg/L. To provide comparative conditions, uridine and thymidine were added, at the start of culture, at concentrations of 7 mg/L and 0.24 mg/L, respectively (these concentrations are the same as those described in Examples of EP 1818392 B1). The culture was continued under each of the different conditions described above until day 14 of culture while a feed medium was added everyday from day 2 of culture. Sampling was done at appropriate timings. Viable cell densities were measured by trypan blue exclusion method, and antibody concentrations were measured by protein A column HPLC. As shown in FIG. 15, in the case of no addition of a nucleic acid component (deoxyuridine, thymidine or deoxycytidine) (control), the highest viable cell density observed during the 14 days of culture was about $16\times10^6$ cells/mL. In contrast, the highest viable cell densities were approximately $21\times10^6$ cells/mL in the case of addition of 25 mg/L deoxyuridine (dU25 mg/L), and about $31\times10^6$ cells/mL in the case of addition of 25 mg/L each of deoxyuridine, thymidine and deoxycytidine (dUdTdC25 mg/L); these values were higher than control. Further, as shown in FIG. 16, in both of the cases of addition of deoxyuridine (dU25 mg/L) and addition of deoxyuridine, thymidine and deoxycytidine (dUdTdC25 mg/L), antibody concentrations remained at higher levels than control. These results suggested that deoxyuridine is capable of enhancing cell growth and antibody production, and that addition of not only deoxyuridine but also thymidine and deoxycytidine produces further enhancing effects on cell growth and antibody production. It was also suggested that the enhancing effects of addition of the three components on cell growth and antibody production are superior to those of addition of 7 mg/L of uridine and 0.24 mg/L of thymidine (reference example).

Example 9

Figure 17:
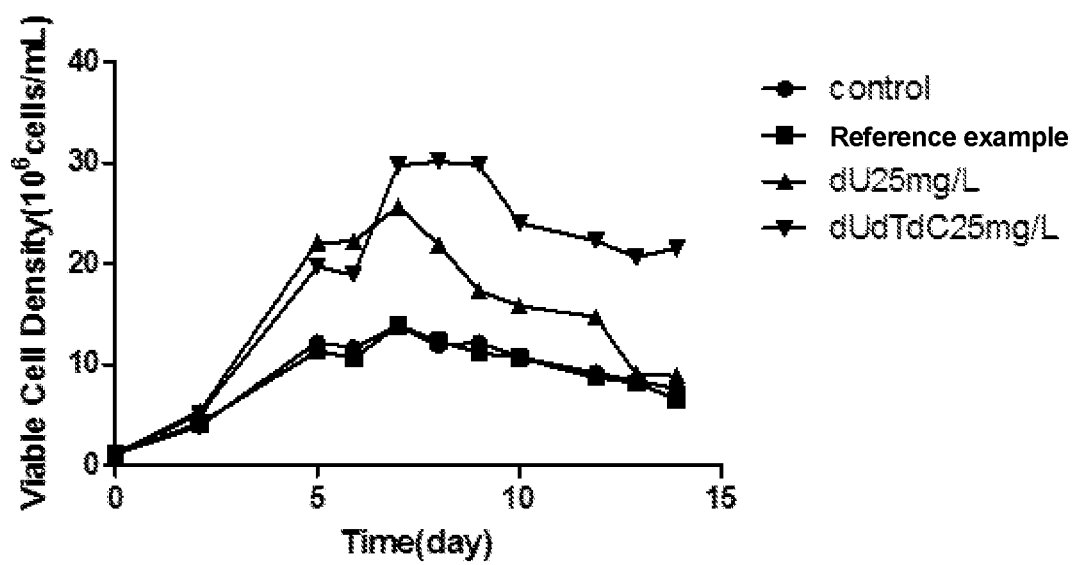
FIG. 17 shows the effects of addition of deoxyuridine, thymidine or deoxycytidine alone, or any combination of them on change in viable cell density during the culture period, with those effects of addition of uridine and thymidine. The vertical axis represents viable cell density ($\times 10^6$ cells/mL), and the horizontal axis represents culture period (days).
Figure 18:
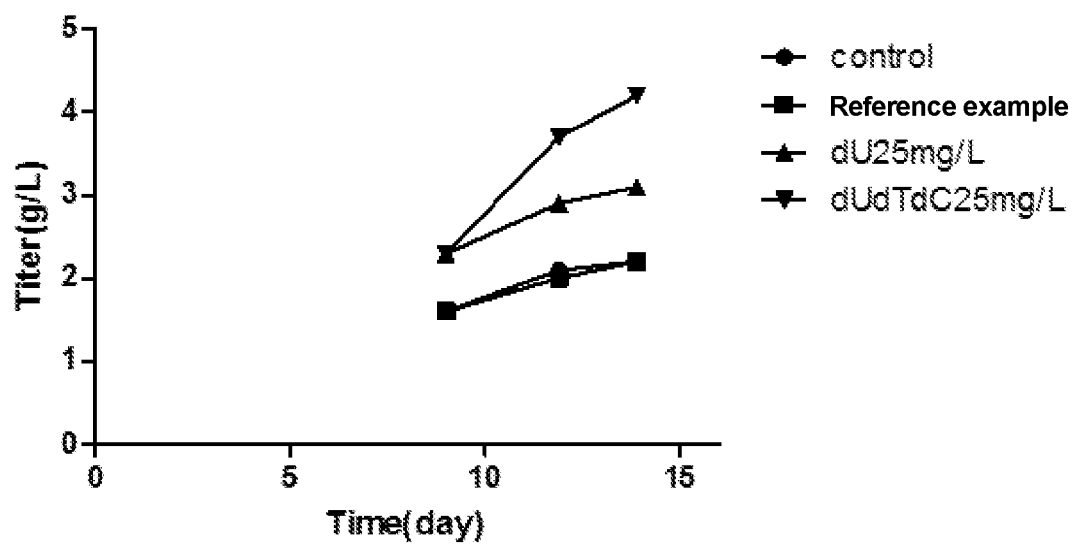
FIG. 18 shows the effects of addition of deoxyuridine, thymidine or deoxycytidine alone or any combination of them on change in produced antibody concentration during the culture period, with those effects of addition of uridine and thymidine. The vertical axis represents produced antibody titer (g/L), and the horizontal axis represents culture period (days).

Effects of Addition of Deoxyuridine, Thymidine and Deoxycytidine in Fed-Batch Culture Using a culture medium for animal cells as a cell growth medium, fed-batch culture of a Fab' fragment-expressing CHO cell line (a CHO cell line in which an anti-human NGF antibody Fab' fragment (1-15 (N52D-A)-Fab') had been expressed, as described in WO 2013/022083) was started at an initial viable cell density of $1\times10^6$ cells/mL under the conditions of 36.5° C. and 5% $CO_2$. At the start of culture, deoxyuridine, thymidine and deoxycytidine were each added to a final concentration of 25 mg/L. To provide comparative conditions, uridine and thymidine were added, at the start of culture, at concentrations of 7 mg/L and 0.24 mg/L, respectively (these concentrations are the same as those described in Examples of EP 1818392 B1). The culture was continued under each of the different conditions described above until day 14 of culture while a feed medium was added everyday from day 2 of culture. Sampling was done at appropriate timings. Viable cell densities were measured by trypan blue exclusion method, and antibody concentrations were measured by reverse-phase HPLC. As shown in FIGS. 17 and 18, in the case of no addition of a nucleic acid component (deoxyuridine, thymidine or deoxycytidine) (control), the highest viable cell density observed during the 14 days of culture was approximately $14\times10^6$ cells/mL, and the protein concentration on the final day of culture was approximately 2.2 g/L. In contrast, in the case of addition of 25 mg/L of deoxyuridine (dU25 mg/L), the highest viable cell density observed during the 14 days of culture was approximately $26\times10^6$ cells/mL, and the protein concentration on the final day of culture was approximately 3.1 g/L; these values were higher than control. Further, in the case of addition of 25 mg/L each of deoxyuridine, thymidine and deoxycytidine (dUdTdC25 mg/L), the highest viable cell density observed during the 14 days of culture was approximately $30\times10^6$ cells/mL, and the protein concentration on the final day of culture was approximately 4.2 g/L; these values were much higher than control and dU25 mg/L. These results suggested that deoxyuridine is capable of enhancing cell growth and antibody production, and that addition of not only deoxyuridine but also thymidine and deoxycytidine produces further enhancing effects on cell growth and antibody production. It was also suggested that the enhancing effects of addition of the three components on cell growth and antibody production are superior to those of addition of 7 mg/L uridine and 0.24 mg/L thymidine (reference example).

The invention claimed is:

1. A method for culturing animal cells in a culture medium, comprising culturing animal cells in a culture medium comprising 25 mg/L of deoxyuridine or a salt thereof, 25 mg/L of thymidine or a salt thereof, and 25 mg/L of deoxycytidine or a salt thereof;
   wherein the animal cells are recombinant Chinese hamster ovary (CHO) cells transformed with a gene encoding an antibody.

2. A method for producing an antibody, the method comprising culturing Chinese hamster ovary (CHO) cells expressing an antibody in a culture medium, wherein the culture medium comprises 25 mg/L of deoxyuridine or a salt thereof, 25 mg/L of thymidine or a salt thereof, and 25 mg/L of deoxycytidine or a salt thereof.

* * * * *